(12) United States Patent
Hoefle et al.

(10) Patent No.: US 7,157,595 B2
(45) Date of Patent: Jan. 2, 2007

(54) DEGRADATION OF EPOTHILONES

(75) Inventors: Gerherd Hoefle, Braunschweig (DE); Usama Karama, Hannover (DE)

(73) Assignee: Helmholtz-Zentrum fur Infektionsforschung GmbH, Braunschweig (DE)

( * ) Notice: Subject to any disclaimer, the term of this patent is extended or adjusted under 35 U.S.C. 154(b) by 234 days.

(21) Appl. No.: 10/468,919

(22) PCT Filed: Feb. 27, 2002

(86) PCT No.: PCT/EP02/02105

§ 371 (c)(1),
(2), (4) Date: Dec. 12, 2003

(87) PCT Pub. No.: WO02/072858

PCT Pub. Date: Sep. 19, 2002

(65) Prior Publication Data

US 2004/0092560 A1     May 13, 2004

(30) Foreign Application Priority Data

Feb. 27, 2001   (EP)   ................................ 01104448

(51) Int. Cl.
    *C07C 69/74*  (2006.01)
(52) U.S. Cl. ...................... 560/126; 548/110
(58) Field of Classification Search ................ 560/126; 548/110
    See application file for complete search history.

(56) References Cited

U.S. PATENT DOCUMENTS

| 5,969,145 A | 10/1999 | Schinzer et al. |
| 6,043,372 A | 3/2000 | Schinzer et al. |
| 6,156,905 A | 12/2000 | Schinzer et al. |
| 6,211,412 B1 | 4/2001 | Georg et al. |
| 6,288,237 B1 | 9/2001 | Hoefle et al. |
| 6,359,140 B1 | 3/2002 | Hofle et al. |
| 6,365,749 B1 | 4/2002 | Kim et al. |
| 6,380,394 B1 | 4/2002 | Nicolaou et al. |
| 6,441,186 B1 | 8/2002 | Nicolaou et al. |
| 6,498,257 B1 | 12/2002 | Vite et al. |
| 6,518,421 B1 | 2/2003 | Li et al. |
| 6,593,115 B1 | 7/2003 | Vite et al. |
| 6,605,599 B1 | 8/2003 | Vite et al. |
| 2005/0090535 A1 | 4/2005 | Reichenbach et al. |

FOREIGN PATENT DOCUMENTS

| EP | 0 057 736 | 8/1982 |
| WO | WO 98/22461 | 5/1998 |

OTHER PUBLICATIONS

Nicolaou et al., "Chemical Biology of Epothilones", Angew. Chem. Int. Ed. 1998, vol. 37, No. 15, pp. 2014-2045.
March, J., "Advanced Organic Chemistry, Reactions, Mechanisms, and Structure", New York, John Wiley & Sons, XP002200250, pp. 1146-1149.
Zhen Yang et al., "Die Totalsynthese von Epothilon A: der Zugang durch Olefinmetathese", Angew. Chem. 1997, vol. 109, No. 1/2, pp. 170-172, XP-002095722.
Smith, A. et al., "Total Synthesis of (−)-Macrolactin A", J. Am. Chem. Soc., 1996, vol. 118, pp. 13095-13096.
U.S. Appl. Ser. No. 09/313,524, filed May 17, 1999, Hoefle et al.

*Primary Examiner*—Joseph K. McKane
*Assistant Examiner*—Robert Shiao
(74) *Attorney, Agent, or Firm*—Anastasia P. Winslow; Gary D. Greenblatt

(57) ABSTRACT

According to one embodiment the invention concerns a process for a degradation of an epothilone C or a epothilone D, wherein an epothilone C or epothilone D is subjected to an olefin metathesis in the presence of ethylene and subsequently an optional ester hydrolysis.

5 Claims, No Drawings

DEGRADATION OF EPOTHILONES

Epothilones of type C and type D belong to the art and are especially characterized by a C=C double bond at positions 12 and 13 and a hydrogen atom at position 12 (type C) or an alkyl group-(type D).

According to one embodiment the invention concerns a process for a degradation of an epothilone C or an epothilone D, wherein an epothilone C or an epothilone D is subjected to an olefin metathesis in the presence of ethylene and subsequently an optional ester hydrolysis (scheme I).

According to the invention the epothilone C or D can be a fermentation product.

According to another embodiment the invention concerns a process for the production of an epothilone of formula 9

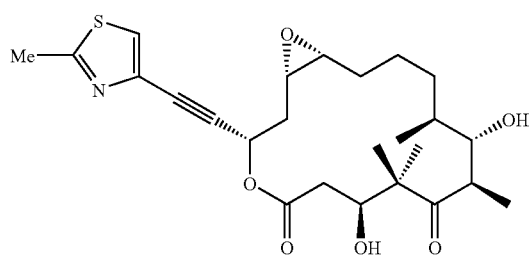

9 wherein an epothilone of formula 2a (schemes I and II) is converted into compound of formula 3a (scheme II), the compound of formula 3a is reacted with a compound of formula 6 (which has been formed by reacting a compound of formula 4 with a compound of formula 5; scheme II) to give a compound of formula 7 by esterification (scheme II), the compound of formula 7 is reacted in the presence of a Grubbs catalyst to give a compound of formula 8a by deprotection (scheme II), the compound of formula 8a is converted into a compound of formula 8b by deprotection (scheme II), and compound of formula 8b is converted to a compound of formula 9 by epoxidation (scheme II).

Alternatively to the reaction sequence depicted in scheme I synthetic intermediates of type 3 may be obtained according to scheme III by
1) cleavage of the lactone of epothilone C or D with e.g. pig liver esterase (PLE) or, after protection of the 3,7-hydroxyl groups, with aqueous base to give 10 (this conversion is described in U.S. patent application Ser. No. 09/811,808, Mar. 19, 2001 by BMS/GBF),
2) optionally esterification with diazomethane and optionally protection of the 3,7-dihydroxyl groups to give 11,
3) olefin metathesis with an excess of an olefin, e.g. ethylene and a ruthenium or molybdenum metathesis catalyst and optionally protection of the 3,7-dihydroxyl groups to give 3b.

EXPERIMENTAL PART

12,13-seco-Epothilone C (2a)

450 mg of epothilone C (1) (0.95 mmol) were dissolved in 250 mL of dichloromethane, saturated with ethylene and after addition of 60 mg of Grubb's catalyst (PhCHRuCl$_2$[P(Cy)$_3$]$_2$ stirred for 24 hours. After addition of further 60 mg of catalyst and stirring for 24 hours the dark solution was evaporated to dryness and the residue purified by chromatography on silica with the solvent system hexanes/tert.-butylmethylester/methanol 80:20:1. The first fraction contained 360 mg (75%) of 2a, the second 100 mg (22%) of recovered starting material 1.

2a: $^1$H-NMR (CDCl$_3$, 300 MHz): δ=6.95 (s, 19-H), 6.02 (s, 17-H), 5.89–5.64 (m, 12-H, 13-H), 5.16–4.89 (m, 12a-H$_2$, 13a-H$_2$), 5.37 (t, J=7 Hz, 15-H), 4.24 (ddd, J=10, 3, 3.5 Hz, 3-H), 3.36 (s, OH), 3.34 (d, J=8 Hz, 7-H), 3.25 (dq, J=1.5, 7 Hz, 8-H), 3.21 (d, J=3.8 Hz, OH), 2.70 (s, 21-H$_3$), 2.52–2.32 (m, 2-H$_2$, 14-H$_2$), 2.07 (d, J=1.5 Hz, 16-Me), 2.05–1.95 (m, 11-H$_2$), 1.8–1.1 (m, 6-H, 8-H, 9-H$_2$, 10-H$_2$), 1.18 (S, 4-Me), 1.10 (s, 4-Me), 1.04 (d, J=7 Hz, 6-Me), 0.83 (d, J=7 Hz, 8-Me).

ESI-MS (pos ions) m/z=506 [M+H$^+$], CI-MS (NH$_3$ pos. ions) m/z=506 [M+H$^+$] (22%), 380 (100%).

3,7-Di-[tert-buthyldimethyl-silyloxy]-4,4,6,8-tetramethyl-5-oxo-12-tridecenoic acid (3a)

To 330 mg (0.65 mmol) of 12,13-seco-epothilone C (2a) dissolved in 10 mL of THF were added with stirring 0.6 mL of NEt$_3$ and 0.6 mL of tert-butyldimethylsilyltriflate. After one hour the solvent was evaporated in vacuo. The residue was dissolved in 10 mL of THF, 70 mg of LiOH dissolved in 0.5 mL of water were added and the mixture stirred for 16 hours. The solvents were evaporated and the residue distributed between phosphate buffer of pH 5 and ethyl acetate. The organic layer was dried with MgSO$_4$ and evaporated to dryness. Preparative HPLC on RP-18 with the solvent system methanol/20 mmol ammonium acetate buffer pH 7 gave 235 mg (67%) of 3a as colorless viscous oil.

Analytical HPLC on Nucleosil RP-18 (260×5 mm) solvent system methanol/20 mmol ammonium acetate buffer pH 7, 1 mL/min, light scattering detector: R$_t$=5.5 min.

$^1$H-NMR (CDCl$_3$, 300 MHz): δ=5.78 (m, 12-H), 4.99, 4.92 (m, 13-H$_2$), 4.39 (dd, J=6.3, 3.4 Hz, 3-H), 3.79 (dd, J=7.2, 2.0 Hz, 7-H), 3.12 (dq, J=7.0 Hz, 8-H), 2.49 (dd, J=16.5, 3.5 Hz, 2-H$_a$), 2.32 (dd, J=16.5, 6.2 Hz, 2-H$_b$), 1.5–1.0 (m, 6-H, 8-H, 9-H$_2$, 10-H$_2$, 11-H$_2$), 1.2 (s, 4-Me), 1.07 (s, 4-Me), 1.04 (d, J=6.9 Hz, 6-Me), 0.91 (d, J=7.0 Hz, 8-Me), 0.89 (s, tBuSi), 0.88 (s, tBuSi), 0.09 (s, MeSi), 0.06 (s, MeSi), 0.05 (s, 2 MeSi).

ESI-MS (neg. ions) m/z=541 (M–H).

4-Bromo-2-methyl-thiazole (4)

1 g (2.05 mmol) 2,4-Dibromothiazole was dissolved in 25 mL anhydrous ether and the resulting solution was stirred under N$_2$ atmosphere at −78° C. To the solution was added n-BuLi (1.1 equivalent, 4.52 mmol, 2.82 mL of 1.6 M solution in hexane) and the stirring was continued for 1 h. To the reaction mixture was then added dropwise a solution of dimethylsulfate 1.16 mL (12.34 mmol) in 1 mL ether. After stirring for 4 h at −78° C. the reaction mixture was allowed to warm to room temperature and stirred for 14 h. The reaction mixture was diluted with a saturated solution of NaHCO$_3$ (10 mL). The aqueous layer was extracted with ether and the combined organic extracts were washed with a brine and dried over MgSO$_4$. Concentration under vacuum, and flash column chromatography (silica gel, 10:1 petroleum ether/ethyl acetate), yielded 0.52 g (70.6%) a yellow oil.

IR (KBr) 3122, 2923, 1485, 1441, 1252, 1178, 1085887, 834 cm$^{-1}$.

$^1$H-NMR (CDCl$_3$, 400 MHz): δ=7.02 (s, 1H), 2.71 (s, 3H).

$^{13}$C-NMR (CDCl$_3$, 100.6 MHz): δ=167.31, 124.18, 116.11, 19.40. EI-MS (70 eV): m/z (%): 179 (93) [M+2H]$^+$, 177 (100) [M+H]$^+$, 169 (30), 164 (20), 159 (15).

HRMS (EI): calcd for C$_4$H$_4$BrNS 176.9251, found 176.9248

1-(2-methyl-thiazol-4-yl)-hex-5-en-1-yn-3-ol (6)

480 mg (2.68 mmol) 4-Bromo-2-methyl-thiazole (4) in 4 mL Et$_3$N was added to 131 mg (0.187 mmol) PdCl$_2$(PPh$_3$)$_2$ and the suspension was stirred 15 minutes under N$_2$ atmosphere at room temperature then 117 mg (0.614 mmol) CuI was added under N$_2$ atmosphere followed by dropwise addition of 283 mg alcohol 5 (A. B. Smith, III et al. *JACS* 120, 3935–3948 (1998)) in 1 mL Et$_3$N. The mixture was stirred for 15 minutes at room temperature and heated to 80° C. for 6 h. Concentration under vacuum, and flash column chromatography (silica gel, 3:2 petroleum ether/ethyl acetate), yielded 0.29 g (56%) a yellow oil. [α]=−29.1 (c=1 in chloroform)

IR (KBr): 3386, 3142, 2924, 1641, 1501, 1435, 1286, 1194, 1041, 993, 918 cm$^{-1}$.

$^1$H-NMR (CDCl$_3$, 400 MHz): δ=7.26 (s, 1H), 5.98–5.88 (m, 1H), 5.23–5.16 (m, 2H), 4.62 (dd, J=11.9, 5.8 Hz, 1H), 2.68 (3H, S), 2.58–2.54 (2H, m), 2.39 (d J=6.1 Hz, 1H, OH)

$^{13}$C-NMR (CDCl3, 75.5 MHz): δ=165.77, 136.20, 133.09, 122.48, 118.85, 89.53, 79.04, 61.84, 41.87, 19.10.

DCI-MS (NH$_3$): 211[M+NH$_4^+$], 194[M+H$^+$].

(1S)-1-[(2-Methyl-thiazole-4-yl)-1-ethynyl]-3-butenyl (3S, 6R, 7S, 8S)-3,7-di-[tert-butyldimethylsiloxy]-4,4,6,8-tetramethyl-5-oxo-12-tridecenoate (7)

99 mg (0.478 mmol)DCC was added at 0° C. to a solution of acid 200 mg(0.368 mmol), alcohol 79 mg (0.405 mmol) and 12 mg (0.09 mmol) DMAP in 10 mL CH$_2$Cl$_2$. The mixture was stirred for 15 min at 0° C. and for 16 h at room temperature. Concentration under vacuum, and flash column chromatography (silica gel, 10:1 petroleum ether/ethyl acetate), yielded 240 mg (91%) a yellow oil.

[α]=−45.8 (c=1 in CH$_2$Cl$_2$)

IR (KBr): 2929, 2856, 1742, 1697, 1641, 1472, 1253, 989 cm$^{-1}$.

$^1$H-NMR (CDCl$_3$, 400 MHz): δ=7.28 (s, 1H, thiazole H-5), 5.91–5.73 (m, 2H, H-12, H-3'), 5.58 (t, J=6.1 Hz, 1H, H-1'), 5.20–4.90 (m, 4H, H-13, H-4'), 4.38 (dd, J=6.3, 3.3 Hz, 1H, H-3), 3.74 (dd, J=6.8, 2.2 Hz, 1H, H-7), 3.11 (dq, J=6.8, 6.8 Hz, 1H, H-6), 2.67 (s, 3H, thiazole CH$_3$), 2.60 (t, J=6.6 Hz, 1H, H-2), 2.55 (dd, J=16.7, 3.5 Hz, 1H, H-2'), 2.29 (dd, J=17.0, 63 Hz, 1H, H-2'), 2.05–1.95 (m, 2H, H-11), 1.47–1.29 (m, 3H,) 1.17–1.08(m, 2H) (H-8, H-9, H-10), 1.21 (s, 3H, H-22), 1.05 (s, 3H, H-23), 1.03 (d, J=6.6 Hz, 3H, C6-CH$_3$), 0.89 (d, J=6.6 Hz, 3H, C8-CH$_3$), 0.88, 0.87(2s, 2x9H, OSiC(CH$_3$)$_3$), 0.089 (s, 3H, OSi(CH$_3$)$_2$), 0.032, 0.028, 0.024 (3s, 3x3H, OSi (CH$_3$)$_2$).

$^{13}$C-NMR (CDCl$_3$, 100.6 MHz): 217.63, 170.84, 165.55, 138.97, 136.08, 132.23, 123.22, 118.91, 114.41, 85.67, 79.97, 73.76, 63.77, 53.38, 45.23, 40.20, 39.09, 38.87, 34.35, 34.00, 30.48, 27.11, 26.26, 26.07, 25.66, 24.97, 23.44, 19.89, 18.55, 17.66, 15.52, −3.61, −3.74, −4.20, −4.59

DCI-MS (NH$_3$): 735[M+NH$_4^+$], 718[M+H$^+$].

HRMS (DCI): calcd for C$_{39}$H$_{70}$N$_2$O$_5$SSi$_2$ 735.4622, found 735.4675.

(4S, 7R, 8S, 9S, 16S)-4,8-Di-tert-butyldimethylsilyloxy-5,5,7,9-tetramethyl-1-6-(2-(2-methyl-1,3-thiazol-4-yl)-1-ethynyl)-1-oxa-13-cyclohexadecen-2,6-dione, mixture of Z and E isomeres (8a)

To a solution of 190 mg (0.264 mmol) diene 7 in 66 mL CH$_2$Cl$_2$ was added 44 mg (0.053 mmol) bis(tricyclohexylphosphine)benzylideneruthenium dichloride and the reaction mixture was stirred for 48 h at room temperature. Concentration under vacuum, and flash column chromatography (silica gel, 10:1 petroleum ether/ethyl acetate), yielded 95 mg (52%) of a yellow oil.

(4S, 7R, 8S, 9S, 16S)-4,8-Dihydroxy-tert-5,5,7,9-tetra-methyl-1-6-[2-(2-methyl-1,3-thiazol-4-yl)-1-ethynyl)-1-oxa-13-cyclohexadecen-2,6-dione (8b), mixture of cis and trans isomere A solution of 95 mg (0.137 mmol) lactone X in 12 mL CH$_x$Cl$_2$ at −20° C. was treated with 2 mL trifluoroacetic acid, and the mixture was stirred for 2 h at 0° C. After concentration under vacuum, the residue was diluted with EtOAC, washed with saturated NaHCO$_3$ solution and dried over MgSO$_4$. Concentration under vacuum, and separation by HPLC (80:20:3 hexane/t-BuOMe/MeOH), yielded 27 mg (42%) of the cis-hydroxy lactone 8b and 27 mg (42%) of the corresponding trans isomer.

[α]=−123 (c=1 in CH$_2$Cl$_2$)

$^1$H-NMR (CDCl$_3$, 400 MHz): δ=7.30 (s, 1H, H-19), 5.65 (dd,J=9.1, 2.9 Hz, 1H, H-15), 5.55–5.41 (m, 2H, H-12, H-13), 4.20 (dd,J=10.8, 2.7 Hz, 1H, H-3), 3.67–3.65 (m, 1H, H-7), 3.12 (dq, J=6.6, 2.0 Hz, 1H, H-6), 2.88–2.77 (m, 1H, H-14), 2.70 (s, 3H, H-21), 2.51 (dd, J=15.0 Hz, 10.9 Hz, 1H, H-2), 2.27 (dd,J=15.2, 2.8 Hz, 1H, H-2), 2.18–2.00 (m, 2H, H-11, H-14), 1.71–1.58 (m, 3H, H-8, H-9, H-10), 1.32 (s, 3H, H-22), 1.30–1.19 (3H, H-8, H-9, H-10), 1.18 (d, J=6.7 Hz, 3H, H-24), 1.07 (s, 3H, H-23), 0.98 (d, J=6.9 Hz, 3H, H-25)

$^{13}$C-NMR (CDCl3, 75.5 MHz): δ=220.81, 169.96, 164.44, 134.16, 134.27, 123.75, 123.00, 86.13, 80.00, 74.38, 72.03, 64.11, 53.31, 41.74, 39.37, 38.71, 32.87, 32.37, 27.63, 27.47, 22.69, 19.18, 18.37, 15.46, 13.70.

16,17-Didehydro-16-desmethyl-epothilone A (9)

To a solution of 27 mg (0.058) of lactone (8b) 4 mL CH$_x$Cl$_2$ was added dropwise at −20° C. a solution of dimethyl dioxirane in acetone (2 equiv). Stirring was continued for 2 h at −20° C. Concentration under vacuum, and separation by HPLC (80:20:3 hexane/t-BuOMe/MeOH), yielded 17 mg (60%) of α-epoxide 9 and 9 mg (32%) of β-epoxide.

α-epoxide

[α]=−34 (c=1 in CH$_2$Cl$_2$)

IR (KBr): 3453, 2958, 2850, 1744, 1690, 1500, 1467, 1376, 1290, 1261, 1147, 979, 775 cm$^{-1}$.

5

$^{13}$C-NMR (CDCl$_3$, 100.6 MHz): 220.55, 170.19, 166.12, 135.50, 123.28, 85.00, 80.56, 75.12, 73.59, 62.71, 57.17, 53.75, 52.67, 43.68, 38.69, 35.96, 32.67, 29.72, 26.56, 23.63, 21.12, 20.48, 19.16, 17.06, 14.46

EI-MS (70 eV): m/z (%): 477(27) [M+H]$^+$, 421 (14), 389 (19), 378 (100), 364 (28), 346 (27), 328 (15).

β-epoxide $^{13}$C-NMR (CDCl$_3$, 75.5 MHz): δ=221.38, 170.03, 166.05, 135.70, 123.28, 85.13, 80.48, 73.24, 73.11, 62.24, 57.14, 55.31, 52.28, 42.89, 38.98, 37.53, 32.40, 31.82, 27.60, 27.01, 23.45, 20.62, 20.36, 16.38, 13.49.

6

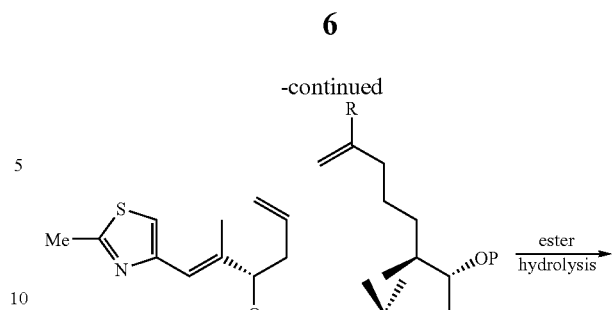

2

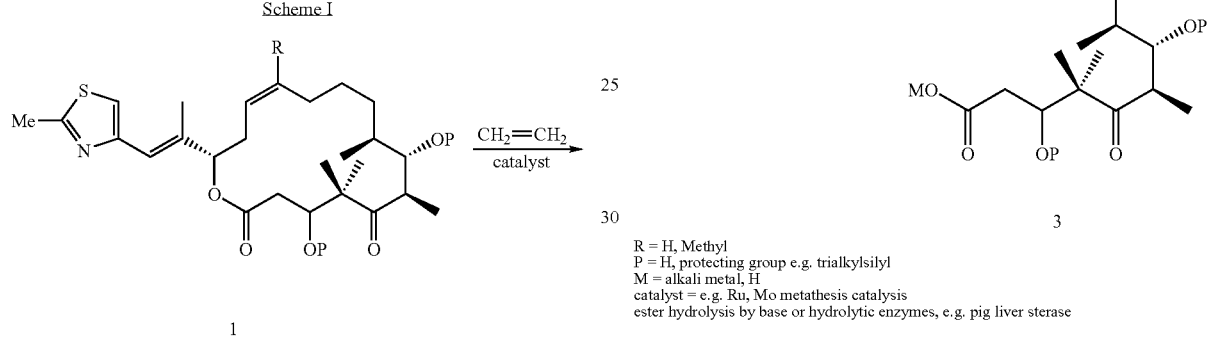

3

R = H, Methyl
P = H, protecting group e.g. trialkylsilyl
M = alkali metal, H
catalyst = e.g. Ru, Mo metathesis catalysis
ester hydrolysis by base or hydrolytic enzymes, e.g. pig liver sterase Scheme I

1

Scheme II

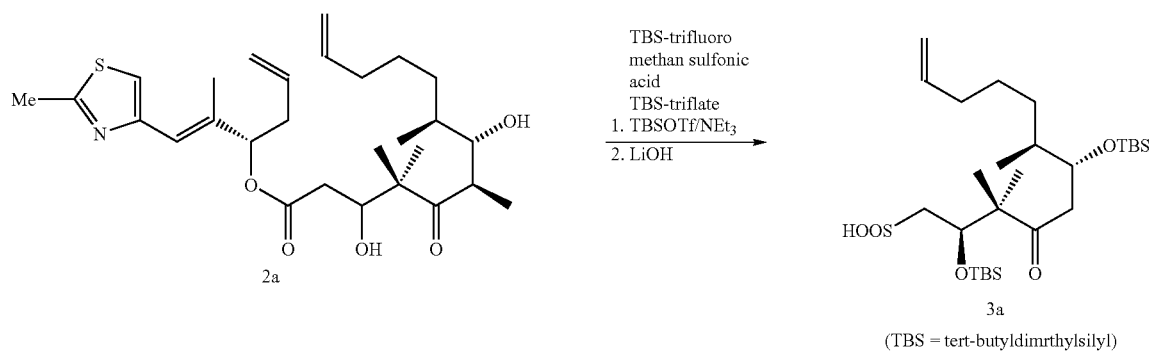

2a → 3a
(TBS = tert-butyldimrthylsilyl)

1. TBSOTf/NEt$_3$
2. LiOH

TBS-trifluoro methan sulfonic acid
TBS-triflate

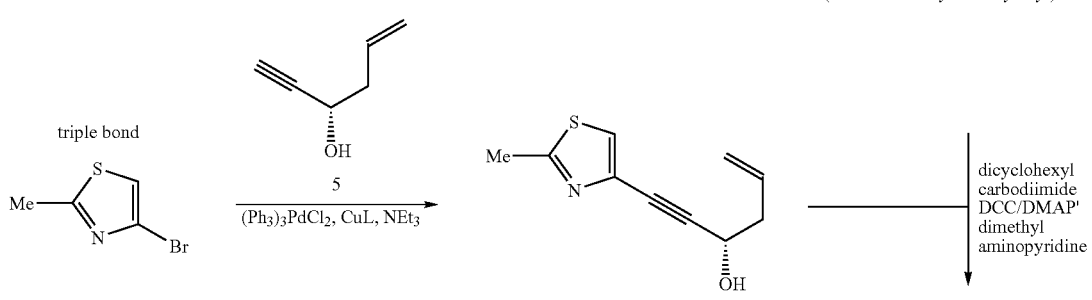

4, 6

(Ph$_3$)$_3$PdCl$_2$, CuL, NEt$_3$ triple bond dicyclohexyl carbodiimide DCC/DMAP' dimethyl aminopyridine

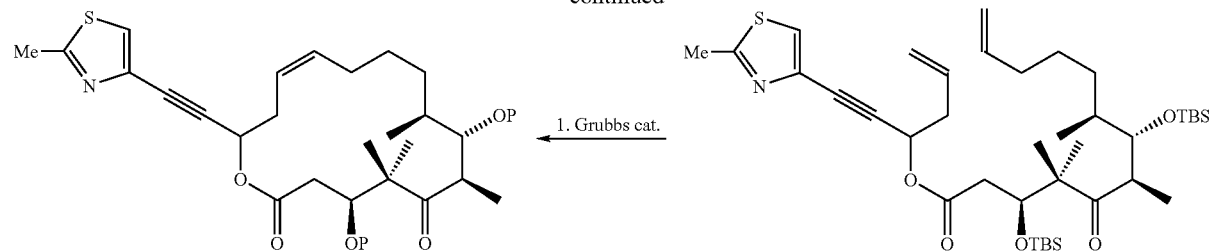
-continued
Grubbs cat.:
RuCl₂(C₆H₅CH)[P(C₆H₁₁)₃]₂
P=TBS   8a
P=H     8b
TFA/CH₂Cl₂
trifluoroacetic acid/
methylene chloride
dimethyldioxirane
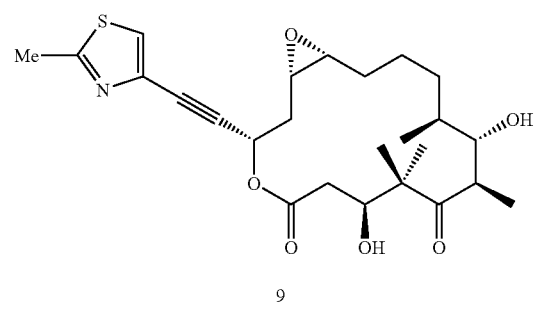
Scheme III
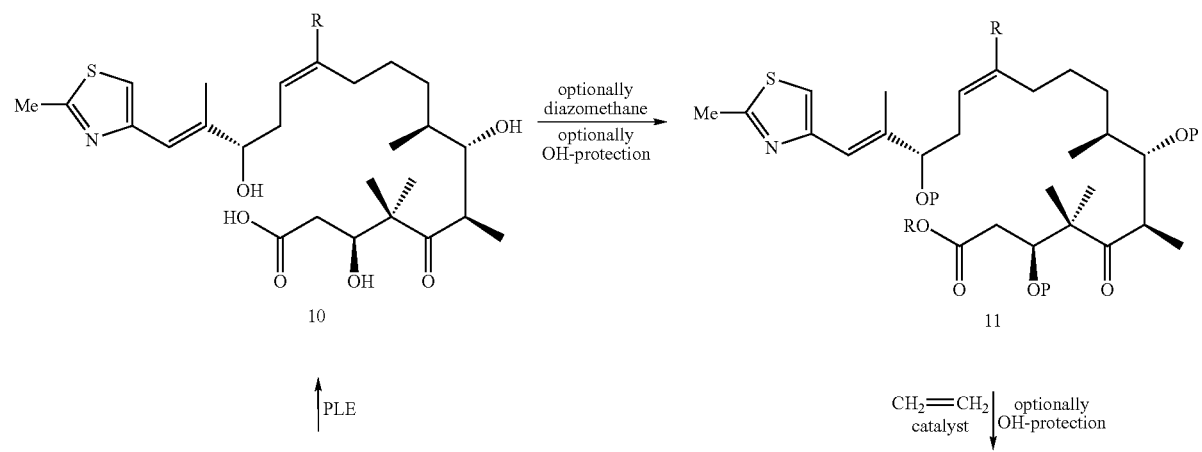

-continued

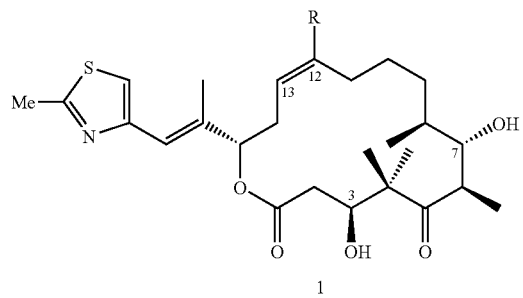

R = H, Methyl
P = H, protecting group e.g. trialkylsilyl, p-methoxybenzyl
catalyst = e.g. Ru, Mo metathesis catalysts
ester hydrolysis by base or hydrolytic enzymes, e.g. pig liver sterase

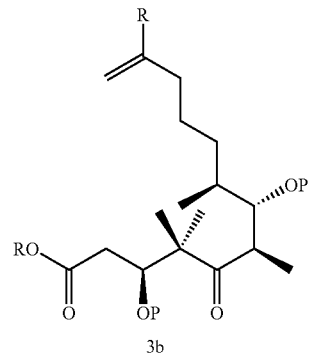

What is claimed is:

1. A process for a degradation of an epothilone C or an epothilone D, comprising subjecting an epothilone compound having the formula,

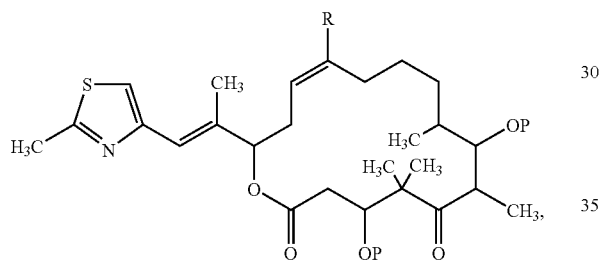

wherein P is a protecting group, and R is hydrogen (epothilone C) or methyl (epothilone D), to an olefin metathesis in the presence of ethylene and catalyst to produce a compound having the formula 2,

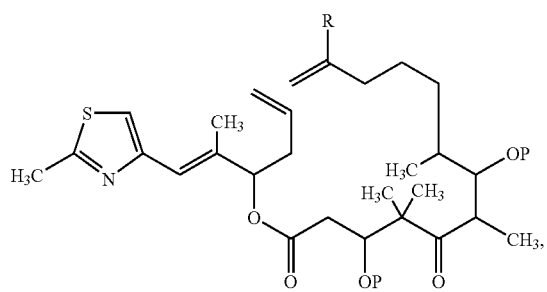

and subsequently performing an ester hydrolysis of the compound of formula 2 in the presence of base or hydrolytic enzymes to produce a compound having the formula 3,

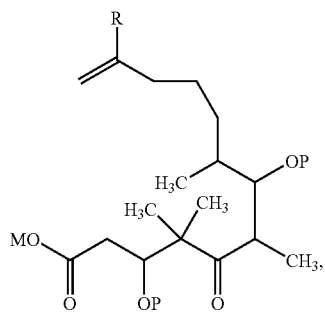

wherein M is an alkali metal or hydrogen.

2. The process according to claim 1, wherein the epothilone C or D is a fermentation product.

3. The process according to claim 1 wherein P is trialkylsilyl or tert-butyl-dimethylsilyl.

4. The process according to claim 1 wherein the catalyst is an Ru and/or Mo metathesis catalyst.

5. The process according to claim 1 wherein the enzyme is pig liver sterase.

* * * * *

UNITED STATES PATENT AND TRADEMARK OFFICE
CERTIFICATE OF CORRECTION

| | | |
|---|---|---|
| PATENT NO. | : 7,157,595 B2 | Page 1 of 1 |
| APPLICATION NO. | : 10/468919 | |
| DATED | : January 2, 2007 | |
| INVENTOR(S) | : Hoefle Gerhard and Karama Usama | |

It is certified that error appears in the above-identified patent and that said Letters Patent is hereby corrected as shown below:

On the Title Page, Item [75] should read:
-- [75] Inventors: Gerhard Hoefle, Braunschweig (DE);
                         Usama Karama, Hannover (DE) --

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,157,595 B2
APPLICATION NO. : 10/468919
DATED : January 2, 2007
INVENTOR(S) : Gerhard Hoefle and Usama Karama It is certified that error appears in the above-identified patent and that said Letters Patent is hereby corrected as shown below:

On the Title Page, Item [75] should read:
-- [75] Inventors: Gerhard Hoefle, Braunschweig (DE);
Usama Karama, Hannover (DE) --

Signed and Sealed this

Twelfth Day of June, 2007

JON W. DUDAS
*Director of the United States Patent and Trademark Office*